(12) United States Patent
Boschi I Llado et al.

(10) Patent No.: US 8,026,397 B2
(45) Date of Patent: Sep. 27, 2011

(54) METHOD FOR OBTAINING AN AMINOINDAN MESYLATE DERIVATIVE

(75) Inventors: Jordi Boschi I Llado, Girona (ES); Maria Carmen Burgarolas Montero, Santa Maria de Paluatordera (ES); Judit Masllorens Llinas, Girona (ES)

(73) Assignee: Medichem, S.A., Barcelona (ES)

( * ) Notice: Subject to any disclaimer, the term of this patent is extended or adjusted under 35 U.S.C. 154(b) by 0 days.

(21) Appl. No.: 12/836,095

(22) Filed: Jul. 14, 2010

(65) Prior Publication Data
US 2010/0280272 A1    Nov. 4, 2010

Related U.S. Application Data

(63) Continuation of application No. 12/470,373, filed on May 21, 2009, now Pat. No. 7,781,616.

(60) Provisional application No. 61/055,849, filed on May 23, 2008.

(51) Int. Cl.
*C07C 211/42*     (2006.01)

(52) U.S. Cl. ..................................... 564/308

(58) Field of Classification Search ......................... None
See application file for complete search history.

(56) References Cited

U.S. PATENT DOCUMENTS
5,532,415 A  *  7/1996  Youdim et al. ............... 564/308
7,781,616 B2    8/2010  Bosch i Llado et al.

FOREIGN PATENT DOCUMENTS
EP       1892233         2/2008
WO       WO95/11016      4/1995
WO       WO2007/061717   5/2007

OTHER PUBLICATIONS

International Search Report for PCT/IB2009/006471, published Feb. 4, 2010.

* cited by examiner

*Primary Examiner* — Brian J Davis
(74) *Attorney, Agent, or Firm* — Cozen O'Connor

(57) ABSTRACT

The invention relates to processes for preparing rasagiline mesylate that avoid the use of alcohol solvents, thereby producing rasagiline mesylate free of any alkyl mesylates, including isopropyl mesylate. The invention further relates to processes for purifying rasagiline mesylate to obtain a product free of alkyl mesylates, and to the thus obtained rasagiline mesylate.

18 Claims, No Drawings

METHOD FOR OBTAINING AN AMINOINDAN MESYLATE DERIVATIVE

CROSS REFERENCE TO RELATED APPLICATIONS

This application is a continuation of U.S. application Ser. No. 12/470,373, filed May 21, 2009 now U.S. Pat. No. 7,781,616 and claims priority to U.S. Provisional Application No. 61/055,849, filed May 23, 2008, which is expressly incorporated herein by reference in its entirety.

BACKGROUND OF THE INVENTION

1. Field of the Invention

The invention relates to a new method for obtaining rasagiline mesylate free of noxious substances and to the obtained rasagiline mesylate.

2. Relevant Background

Rasagiline mesylate is an active pharmaceutical substance with an empirical formula of $C_{12}H_{13}N.CH_4O_3S$ and a molecular weight of 267.34. Rasagiline mesylate is the international common accepted name for R-(+)-N-propargyl-1-aminoindan mesylate, which is represented in Formula I.

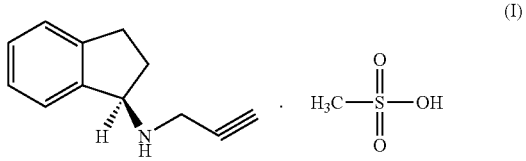

(I)

Rasagiline mesylate is an active substance indicated for the treatment of the signs and symptoms of idiopathic Parkinson disease as initial monotherapy and as adjunct therapy to levodopa. Rasagiline is a selective irreversible inhibitor of the B-form of monoamine oxidase enzyme (MAO-B). In the United States, rasagiline mesylate is marketed under the name Azilect™ for the treatment of early Parkinson disease.

The preparation of rasagiline mesylate is described in U.S. Pat. No. 5,532,415. In that patent, the product is obtained by treating the enantiopure rasagiline L-tartrate salt with methanesulfonic acid in isopropanol at reflux temperature.

International patent application publication No. WO 2007/061717 describes an alternative conversion of rasagiline L-tartrate to rasagiline mesylate. In particular, Example 17 of this reference describes the preparation of rasagiline mesylate by isolating rasagiline base from rasagiline tartrate, followed by treating the obtained rasagiline base with methanesulfonic acid in isopropanol at reflux temperature.

SUMMARY OF THE INVENTION

The preparation and/or crystallization of mesylate salts of amino drug compounds in alcoholic solvents may lead to the formation of alkyl mesylates that are known to be noxious substances and genotoxic compounds.

The processes described in the prior art for preparing rasagiline mesylate, all of which make use of isopropanol as a solvent, may lead to the formation of isopropyl mesylate, an alkyl mesylate which, based on the Ames test and other genotoxicity studies, has been described to show potential genotoxic properties. More precisely, the applicants have carried out some crystallizations of rasagiline mesylate in isopropanol and have detected the presence of isopropyl mesylate.

Thus, the use of alcoholic solvents for the preparation and/or purification of a mesylate salt of a compound that is intended for use as an active pharmaceutical ingredient is far from ideal.

As described herein, the applicants have developed processes to obtain and/or purify rasagiline mesylate that completely avoid the use of any alcoholic solvent. In this way it is guaranteed that alkyl mesylates are not formed neither during the preparation and/or purification of the rasagiline mesylate salt nor during its shelf life, and hence will not contaminate the rasagiline mesylate thus obtained.

In a first aspect, the present invention relates to a process for preparing rasagiline mesylate,

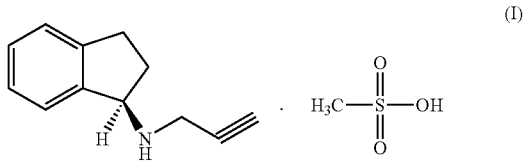

(I)

said process comprising treating rasagiline free base, or an acid addition salt thereof, wherein the rasagiline acid addition salt is the salt of an acid weaker than methanesulfonic acid, with methanesulfonic acid and in the presence of a non-hydroxylic solvent.

The rasagiline acid addition salt wherein the salt is the salt of an acid weaker than methanesulfonic acid may be any salt which may be able to produce the methanesulfonic acid addition salt of rasagiline (i.e. rasagiline mesylate) by means of an anionic interchange with methanesulfonic acid. Preferably, the rasagiline acid addition salt of an acid weaker than methanesulfonic acid is rasagiline tartaric acid addition salt.

The non-hydroxylic solvent of the preparation process is preferably acetonitrile, toluene, or mixtures thereof. More preferably, the non-hydroxylic solvent is a mixture of toluene and acetonitrile.

In another aspect, the present invention relates to a process for purifying rasagiline mesylate (I), said process comprising treating rasagiline mesylate in the presence of a non-hydroxylic solvent. The treatment of the rasagiline mesylate in the presence of a non-hydroxylic solvent preferably comprises crystallizing the rasagiline mesylate from a non-hydroxylic solvent. The non-hydroxylic solvent of the treatment process is preferably acetonitrile, toluene, or mixtures thereof. More preferably, the non-hydroxylic solvent is acetonitrile.

In another further aspect, the present invention relates to a process for preparing purified rasagiline mesylate (I), said process comprising (i) preparing rasagiline mesylate according to the preparation process of the invention, and (ii) treating the rasagiline mesylate according to the purification process of the invention at least one time, to improve the chemical quality of the product.

In one embodiment, the process of the invention above for preparing rasagiline mesylate comprises (i) treating rasagiline free base with methanesulfonic acid and in the presence of toluene as a solvent, and (ii) treating the thus obtained rasagiline mesylate to improve its chemical quality by means of (ii)(a) dissolving the rasagiline mesylate in acetonitrile and treating the solution with activated charcoal, and (ii)(b) crystallizing the rasagiline mesylate from acetonitrile.

In an alternative embodiment, the process above for preparing rasagiline mesylate of the invention comprises (i) treating rasagiline free base with methanesulfonic acid and in the presence of a solvent comprising a mixture of toluene with acetonitrile, and (ii) treating the thus obtained rasagiline mesylate to improve the chemical quality of the product by means of crystallizing the rasagiline mesylate from acetonitrile.

The applicants have surprisingly observed that if the preparation process of the processes of the invention is carried out in a mixture of toluene with acetonitrile instead of toluene alone, the preparation is more efficient. Namely, the said process affords rasagiline mesylate with good yield (i.e. greater than 86%) and with high chemical purity (i.e. greater than 99%, as measured by HPLC). By treating the obtained rasagiline mesylate according to the purification process of the invention to improve the chemical quality of the product, the rasagiline mesylate is obtained with a chemical purity higher than 99.9%, as measured by HPLC.

The applicants have also found that the rasagiline mesylate obtained according to the preparation and/or purification processes of the invention shows improved properties since does not entail toxic problems associated with the presence of isopropyl mesylate. Namely, the rasagiline mesylate obtained according to the preparation and/or purification processes of the invention is free of isopropyl mesylate. Also, since the rasagiline mesylate obtained according to the preparation and/or purification processes of the invention does not contain residual alcoholic solvent(s), the formation of isopropyl mesylate cannot occur during the product shelf life.

The various embodiments of the invention having thus been generally described, several examples will hereafter be discussed to illustrate the inventive aspects more fully.

DETAILED DESCRIPTION OF THE PREFERRED EMBODIMENTS

Reference will now be made in detail to the preferred embodiments of the invention. This invention may, however, be embodied in many different forms and should not be construed as limited to the embodiments set forth herein.

It will be apparent to those skilled in the art that various modifications and variations can be made in the present invention and specific examples provided herein without departing from the spirit or scope of the invention. Thus, it is intended that the present invention covers the modifications and variations of this invention that come within the scope of any claims and their equivalents.

The invention will now be described in more detail by way of examples. The following examples are for illustrative purposes only and are not intended, nor should they be interpreted, to limit the scope of the invention.

SPECIFIC EXAMPLES

General Experimental Conditions

HPLC Method

The chromatographic separation was carried out in a Chiralpak IC, 5 µm, 250×4.6 mm I.D column; at 30° C.

The mobile phase was prepared by mixing 950 mL of n-hexane, 40 mL of 2-propanol, 10 mL of ethanol, 4 mL of trifluoroacetic acid and 1 mL of diethylamine. The mixture was mixed thoroughly.

The chromatograph was equipped with a 265 nm detector and the flow rate was 1.4 mL per minute.

The test samples were prepared by dissolving the appropriate amount of sample to obtain 10 mg per mL in diluent. The diluent was prepared by mixing 89 mL of mobile phase, 10 mL of 2-propanol and 1 mL of diethylamine. The injection volume was 5 µL.

GC Method

The GC analysis was performed on an Agilent 6890N. The following parameters were used: Gas carrier: He; Column head pressure: 10 psi (constant pressure); Split ratio: 2:1, Injector Temp.: 250° C.; Detector Temp. (FID): 300° C.; Column: HP-1 (100% dimethyl polysiloxane), 50 m length, 0.32 mm internal diameter, 1.05 µm film thickness.

The following temperature program was used: Initial Temp.: 100° C.; Initial time: 5 min; Rate 1: 10° C./min; Final Temp. 1: 200° C.; Final time 1: 10 min; Rate 2: 10° C./min Final Temp. 2: 290° C.; Final time 2: 15 min. Injection volume: 4 µL (Agilent 7683B autosampler).

Sample preparation for mother liquor: analyzed directly, without further treatment.

Sample preparation for solid: 100 mg of sample were weighed and dissolved with 2 mL of water. 2 mL of dichloromethane were added and the mixture was shaken vigorously for 15 minutes. The phases were allowed to separate for 15 minutes. The organic phase was transferred to a centrifuge tube containing approximately 50 mg of $Na_2CO_3$. The mixture was shaken and centrifuged for 10 min. An aliquot of the mixture was transferred to a suitable vial and was analyzed by GC.

Approximate GC Retention Time for isopropyl mesylate: 13.1 minutes.

Example 1

Preparation of Rasagiline Mesylate

Step (a): Preparation of Rasagiline Base

In a 250 mL round-bottomed flask placed in a water/ice bath were charged 23.81 g of (R)-1-aminoindan and 60.95 mL of water. Subsequently, 15.74 g of 50% NaOH aqueous solution were added. After this addition, 71.43 mL of toluene and 35.08 g of propargyl benzenesulfonate were added onto the reaction mixture. A biphasic brown solution was thus obtained.

The reaction mixture was heated to 45-50° C. and stirred for 4 hours at this temperature. After cooling to about 20-25° C., the mixture was allowed to stand and the resulting two phases were separated. 38.81 mL of water were added to the separated organic phase and pH was adjusted to 6-7 with 35% HCl solution (3 mL were needed). The mixture was allowed to stand and the resulting two phases were separated.

1.53 g of active charcoal and anhydrous sodium sulphate were added to the toluenic phase, stirred for 10-15 minutes and filtered, washing the filter with 5 mL of toluene. This solution contained 22.19 g of rasagiline base (yield: 72.49%).

Step (b): Preparation of Rasagiline Mesylate

The toluenic phase of step (a) was charged into a 250 mL round-bottomed flask placed in a water/ice bath and equipped with mechanical stirrer. 9.25 mL of methanesulfonic acid were added in about 10-15 minutes, while maintaining the temperature below 22° C. After the addition, the reaction mixture was stirred for an additional 1 hour at 20-25° C. The mixture was then filtered and the filter was washed twice with 10.4 mL of toluene. 41.12 g of wet crude product were obtained (29.64 g of dry crude, partial yield: 85.54%; 79.65% by HPLC).

Step (c): Purification of Rasagiline Mesylate

In a 250 mL round-bottomed flask were charged the wet crude product obtained in step (b) above and 177.80 mL of acetonitrile. The suspension was heated to reflux until almost complete dissolution was observed. 1.47 g of activated charcoal were added and the resulting mixture was stirred for 10-15 minutes at this temperature. The mixture was then cooled to 70-75° C. and filtered. Partial precipitation occurred, and the suspension was heated to reflux temperature to re-dissolve the solid. The solution was then allowed to cool over about 50-60 minutes to 20-25° C. and stirred at this temperature for 2-3 hours. The suspension was filtered, and the collected solid was washed with 15.8 mL of acetonitrile. 21.38 g of an almost white solid were obtained after drying (partial yield 72.16%; 99.84% by HPLC).

The above product was crystallized again from 128.28 mL of acetonitrile at reflux temperature. Filtration of the hot reaction mixture was performed to eliminate any residual mechanical particulates or active charcoal. The solution was then allowed to cool to 20-25° C. and subsequently stirred for 2 hours at this temperature. The suspension was filtered and the collected solid was washed twice with 16 mL of acetonitrile. 19.10 g of a white solid were obtained after drying (partial yield: 89.35%; 100.0% by HPLC).

The solid collected was suspended in 57.3 mL of acetonitrile/water (95:5) and stirred for 2 hours at 20-25° C. The suspension was then filtered, and the collected solid was washed twice with 5.6. mL of the solvent mixture. 10.75 g of a white solid were obtained after drying (partial yield: 56.29%, Global yield: 22.50%; 99.99 by HPLC; Assay by HPLC 100.2%; potentiometric assay using tetrabutyl ammonium hydroxide: 100.28%; Specific optical rotation (2% ethanol, 20° C.: +21.46°).

Example 2

Preparation of Rasagiline Mesylate

Step (a): Preparation of Rasagiline Base
In a 500 mL round-bottomed flask placed in a water/ice bath were charged 35 g of (R)-1-aminoindan and 89.60 mL of water. Subsequently, 23.12 g of 50% NaOH solution were added without exceeding 20-25° C., followed by 105 mL of toluene. After these additions, 41.15 mL of propargyl benzenesulfonate were charged onto the reaction mixture over a period of 10 minutes. A biphasic brown solution was thus obtained.

The reaction mixture was heated to 45-50° C. and stirred for 4 hours at this temperature. After cooling to about 20-25° C., the mixture was allowed to stand, and the resulting two phases were separated. 101.15 mL of water was added to the separated organic phase, and the pH was adjusted to 6-7 with 35% HCl solution (6 mL were needed). The mixture was allowed to stand, and the resulting two phases were separated. Over the toluenic phase were added 101.15 mL of water, stirred 10 minutes, let to decant, and the two phases separated.

2.25 g of active charcoal and anhydrous sodium sulphate were added to the toluenic phase, stirred for 10-15 minutes and filtered, washing the filter with 5 mL of toluene. This solution contained 30.52 g of rasagiline base (yield: 67.82%).

Step (b): Preparation of Rasagiline Mesylate
The toluenic phase of step (a) was charged into a 500 mL round-bottomed flask placed in a water/ice bath and equipped with mechanical stirrer. 12.68 mL of methanesulfonic acid were added in about 10-15 minutes, maintaining the temperature below 22° C. After the addition, the reaction mixture was stirred for 1 hour at 20-25° C. The mixture was then filtered, and the filter was washed twice with 10.1 mL of toluene. 55.38 g of wet crude product were obtained (46.40 g of dry crude, partial yield: 97.39%; 73.52% by HPLC).

Step (c): Purification of Rasagiline Mesylate
In a 500 mL round-bottomed flask were charged the wet crude product obtained in step (c) above and 278.4 mL of acetonitrile. The suspension was heated to reflux until almost complete dissolution was observed. 2.32 g of activated charcoal were then added, and the resulting mixture was stirred for 10-15 minutes at this temperature. The mixture was then cooled to 70-75° C. and filtered. Partial precipitation occurred, and the suspension was heated to reflux temperature to re-dissolve the solid. The solution was then allowed to cool over about 50-60 minutes to 20-25° C. and stirred at this temperature for 2-3 hours. The suspension was filtered, and the collected solid was washed twice with 15.4 mL of acetonitrile. 28.0 g of an almost white solid were obtained after drying (partial yield 56.63%; 99.78% by HPLC).

The above product was crystallized again from 105.16 mL of acetonitrile at reflux temperature. Filtration of the reaction mixture was performed to eliminate any residual mechanical particulates or active charcoal. The solution was then allowed to cool to 20-25° C. and subsequently stirred for 2 hours at this temperature. The suspension was filtered, and the collected solid was washed twice with 5.3 mL of acetonitrile. 23.32 g of a white solid were obtained after drying (partial yield: 88.74%; global yield 32.80%; 99.96% by HPLC, Assay by HPLC 100.57%).

Example 3

Preparation of Rasagiline Mesylate

Step (a): Preparation of Rasagiline Base
In a 1 L round-bottomed flask under nitrogen and equipped with mechanical stirring, were charged 55.00 g of (R)-1-aminoindan, 165 mL of toluene and 147 mL of water. The mixture was stirred at 20-25° C., and subsequently 36.34 g of 50% aqueous NaOH solution were added dropwise without exceeding 30° C. Once the addition was complete, 81.03 g of propargyl benzenesulfonate were added dropwise to the reaction mixture maintaining the temperature below 30° C. A biphasic brown solution was obtained.

The reaction mixture was heated to 45-50° C. and stirred for 4 hours at this temperature. After this period of time, the mixture was cooled down to 20-25° C. and was allowed to stand. The two phases were then separated. 110 mL of toluene and 165 mL of water were added to the stirred organic phase, and the pH was adjusted to 7.5±0.2 by the dropwise addition of 35% aqueous HCl solution (5.50 g were required). 4.125 g of celite were then added, the mixture was stirred for 20 min at 20-25° C. and then filtered, washing the filter cake with 2×15 mL of toluene. The filtrate was allowed to stand, and the phases were separated. 165 mL of water were then added to the organic phase, and the pH was adjusted to 7.5±0.2 by the dropwise addition of 35% aqueous HCl solution (0.62 g were required). The mixture was stirred for 10 min, and then the phases were separated.

5.00 g of anhydrous sodium sulphate were added to the toluenic phase, the mixture was stirred for 1 h at 20-25° C. and filtered, washing the filter cake with 2×15 mL of toluene. The resultant toluenic solution contained 52.72 g of rasagiline base (yield: 74.56%).

Step (b): Preparation of Rasagiline Mesylate
The toluenic phase of step (a) was charged into a 500 mL round-bottomed flask under nitrogen and equipped with mechanical stirring. 110 mL of acetonitrile were then added, followed by the dropwise addition of 32.54 g of methanesulfonic acid in about 20 minutes, maintaining the temperature below 40° C. Precipitation started after the addition of approximately 10% of the total amount of methanesulfonic acid. The thick suspension thus obtained was heated up to 75-80° C. and stirred for 30 min. The suspension was then cooled down to 10-15° C., stirred for at least 1 hour and filtered. The collected solid was washed with 3×20 mL of acetonitrile to yield 74.27 g of yellowish wet product (70.95 g of dry crude, partial yield: 86.20%; 99.32% by HPLC).

Step (c): Purification of Rasagiline Mesylate

The wet crude obtained in step (b) was charged into a 500 mL round-bottomed flask together with 426 mL of acetonitrile. The suspension was heated up to reflux until complete dissolution occurred, cooled down to 20-25° C. and stirred for 1 hour, cooled down further to 0-5° C. and stirred for at least 1 hour more. The suspension was then filtered, and the collected solid was washed with 2×55 mL of acetonitrile to give 67.38 g of white wet product (65.76 g of dry crude, partial yield 92.68%; 99.93% by HPLC).

Example 4

Crystallization of Rasagiline Mesylate in Isopropanol 2 g of rasagiline mesylate, 8 mL of isopropanol and 0.14 g of methanesulfonic acid were heated to reflux until complete dissolution occurred, and the mixture was stirred at reflux. After a period of time, the mixture was allowed to cool to 0-5° C., the obtained suspension was filtered, and the collected solid was washed with 1.5 mL of isopropanol.

According to the GC method, isopropyl mesylate was detected as a by-product (solid and mother liquors were tested).

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

The invention claimed is:

1. Rasagiline mesylate free of hydroxylic solvents.
2. The rasagiline mesylate of claim 1, wherein the hydroxylic solvent is isopropanol.
3. The rasagiline mesylate of claim 2, wherein the rasagiline mesylate is also free of isopropyl mesylate.
4. The rasagiline mesylate of claim 1, wherein the rasagiline mesylate has a chemical purity higher than 99.9%.
5. Rasagiline mesylate free of alkyl mesylates.
6. The rasagiline mesylate of claim 5, wherein the rasagiline mesylate has a chemical purity higher than 99.9%.
7. The rasagiline mesylate of claim 5, wherein the alkyl mesylate is isopropyl mesylate.
8. Rasagiline mesylate free of alkyl mesylates made by the process comprising:
    treating at least one of rasagiline free base and an acid addition salt thereof with methanesulfonic acid and in the presence of a non-hydroxylic solvent.
9. The rasagiline mesylate of claim 8, wherein the non-hydroxylic solvent is a mixture of acetonitrile and toluene.
10. Rasagiline mesylate free of alkyl mesylates made by the process comprising:
    contacting rasagiline mesylate with a non-hydroxylic solvent.
11. The rasagiline mesylate of claim 10, wherein the contacting comprises crystallizing rasagiline mesylate from acetonitrile.
12. A composition comprising:
    rasagiline mesylate,
    wherein the composition is free of hydroxylic solvents.
13. The composition of claim 12, wherein the hydroxylic solvent is isopropanol.
14. The composition of claim 13, wherein the composition is free of isopropyl mesylate.
15. A composition comprising:
    rasagiline mesylate,
    wherein the composition is free of alkyl mesylates.
16. The composition of claim 15, wherein the composition is free of isopropyl mesylate.
17. An active pharmaceutical ingredient consisting of rasagiline mesylate free of alkyl mesylates and hydroxylic solvents.
18. The active pharmaceutical ingredient of claim 17, wherein the rasagiline mesylate is free of isopropyl mesylate.

* * * * *